United States Patent [19]

Shoesmith, deceased

[11] Patent Number: Plant 6,398

[45] Date of Patent: Nov. 15, 1988

[54] CHRYSANTHEMUM PLANT NAMED VOLUNTEER

[75] Inventor: Leonard H. Shoesmith, deceased, late of Westfield, England, by May Victoria Shoesmith, executrix

[73] Assignee: Ball Pan Am Plant Co., Parrish, Fla.

[21] Appl. No.: 5,761

[22] Filed: Jan. 21, 1987

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named volunteer characterized by its white ray florets and yellow-green anemone disc, compact and freely branching growth habit, 8½ week response, and by its adaptability to production in 4½" pots or as a garden mum.

1 Drawing Sheet

The present invention comprises a new and distinct cultivar of *Chrysanthemum morifolium,* Ramat., hereinafter referred to by the cultivar name Volunteer.

Volunteer is a product of a planned breeding program which had the objective of creating new Chrysanthemum cultivars having the characteristics of free branching, compact growth habit, anemone flower type, clear white ray floret color with yellow-green disc florets, and suitability for production in 4½ pots or as a garden mum. Such traits in combination were not present or needed improvement in previously available commercial cultivars.

Volunteer was originated from a hybridization made in a controlled breeding program in Westfield-Woking, England by Leonard H. Shoesmith in 1980. The male and female parents are unknown at this time. Volunteer was discovered and selected as one flowering plant within the progeny of the stated parentage by Leonard H. Shoesmith in November 1981 in a controlled environment in Parrish, Fla.

The first act of asexual reproduction of Volunteer was accomplished when vegetative cuttings were taken from the initial selection in February 1982 in a controlled environment in Parrish, Fla. by a technician working under formulations established and supervised by Leonard H. Shoesmith. Horticultural examination of selected units initiated in April 1982 has demonstrated that the combination of characteristics as herein disclosed for Volunteer are firmly fixed and are retained through successive generations of asexual reproduction.

Volunteer has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

The following traits have been repeatedly observed and are determined to be basic characteristics of Volunteer, which in combination distinguish this Chrysanthemum as a new and distinct cultivar:

1. Clear white ray florets surrounding a yellow anemone type disc.
2. Approximately 42 ray florets per capitulum.
3. Mature capitulum is 50–55 mm in diameter.

4. Individual ray florets approximately 24 mm long×6 mm wide.
5. 8½ week flowering response.
6. Compact, freely branching growth habit, suitable for production in 4½" pots or as a garden variety.
7. Anemone disc florets are yellow-green when immature, changing to yellow when mature.

The accompanying photographic drawing shows in perspective view typical inflorescence and foliage characteristics of Volunteer. The photograph is in black and white, with the white ray florets closely corresponding in color to the actual white ray floret color. Several disc florets have been colored to depict immature and mature disc floret color.

In the following description, color references are made to The Royal Horticultural Society Colour Chart. The color values were determined at approximately 2:00 p.m. in September 1986 under fluorescent light at Parrish, Fla.

Classification:

*Botanical.*—*Chrysanthemum morifolium,* Ramat., cv Volunteer.

*Commercial.*—Garden or pot mum.

INFLORESCENCE

A. Capitulum:

*Form.*—Flat.

*Type.*—Anemone.

*Diameter across face.*—50–55 mm.

B. Corolla of ray florets:

*Color (general tonality from a distance of three meters).*—White.

*Color (upper surface).*—White.

*Color (under surface).*—White.

C. Corolla of disc florets:

*Color* (mature).—Yellow 1B.

*Color (immature).*—Approximately 154A.

D. Reproductive organs:

*Androecium.*—Present in anemone disc florets only.

*Gynoecium.*—Present in all ray and anemone disc florets.

PLANT

A. General appearance:

*Height.*—19 cm when grown in a 4½" pot. Height can differ depending upon growing conditions, B-Nine applications and scheduling practices.

B. Foliage:

*Color (upper surface).*—147A.

*Color (under surface).*—147B.

*Shape.*—Ovate with cleft margins.

I claim:

1. A new and distinct cultivar of Chrysanthemum plant named Volunteer, as described and illustrated, and particularly characterized by its white ray florets and yellow-green anemone disc, compact and freely branching growth habit, 8½ week response, and by its adaptability to production in 4½" pots or as a garden mum.

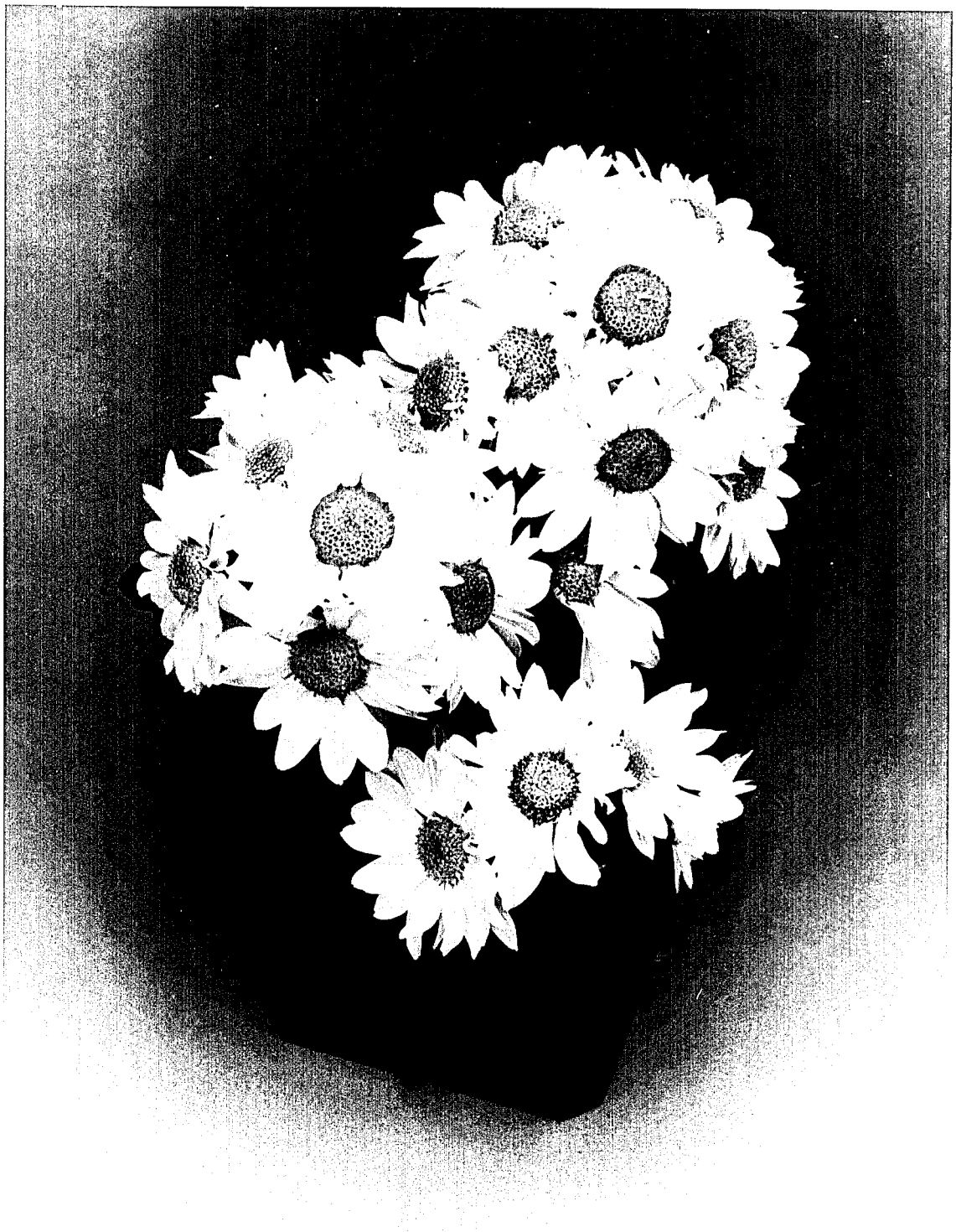

* * * * *